(12) United States Patent
Lee et al.

(10) Patent No.: US 11,747,318 B2
(45) Date of Patent: Sep. 5, 2023

(54) RESIN COMPOSITION AND RELIABILITY EVALUATION METHOD THEREOF AND COLOR CONVERSION FILM COMPRISING THE SAME

(71) Applicant: LG CHEM, LTD., Seoul (KR)

(72) Inventors: Jeong Yong Lee, Daejeon (KR); Ji Eun Kim, Daejeon (KR); Seung Ha Kim, Daejeon (KR); Hye Jin Han, Daejeon (KR); Dong Wook Lee, Daejeon (KR); Myung Han Lee, Daejeon (KR)

(73) Assignee: LG CHEM, LTD., Seoul (KR)

( * ) Notice: Subject to any disclaimer, the term of this patent is extended or adjusted under 35 U.S.C. 154(b) by 800 days.

(21) Appl. No.: 16/614,687

(22) PCT Filed: May 21, 2018

(86) PCT No.: PCT/KR2018/005766
§ 371 (c)(1),
(2) Date: Nov. 18, 2019

(87) PCT Pub. No.: WO2018/212633
PCT Pub. Date: Nov. 22, 2018

(65) Prior Publication Data
US 2020/0182854 A1 Jun. 11, 2020

(30) Foreign Application Priority Data
May 19, 2017 (KR) .................. KR10-2017-0062427

(51) Int. Cl.
| | |
|---|---|
| *G01N 33/44* | (2006.01) |
| *C08L 33/10* | (2006.01) |
| *C08K 5/00* | (2006.01) |
| *C08K 5/01* | (2006.01) |
| *C08K 5/13* | (2006.01) |
| *C08K 5/1545* | (2006.01) |
| *C08K 5/3415* | (2006.01) |
| *C08K 5/3432* | (2006.01) |
| *C08K 5/3445* | (2006.01) |
| *C08K 5/3492* | (2006.01) |
| *C08L 25/06* | (2006.01) |
| *C08L 27/16* | (2006.01) |
| *C08L 31/04* | (2006.01) |
| *C08L 33/08* | (2006.01) |
| *G01N 21/64* | (2006.01) |
| *H10K 50/00* | (2023.01) |

(52) U.S. Cl.
CPC ......... *G01N 33/442* (2013.01); *C08K 5/0025* (2013.01); *C08K 5/0041* (2013.01); *C08K 5/01* (2013.01); *C08K 5/13* (2013.01); *C08K 5/1545* (2013.01); *C08K 5/3415* (2013.01); *C08K 5/3432* (2013.01); *C08K 5/3445* (2013.01); *C08K 5/34924* (2013.01); *C08L 25/06* (2013.01); *C08L 27/16* (2013.01); *C08L 31/04* (2013.01); *C08L 33/08* (2013.01); *C08L 33/10* (2013.01); *G01N 21/64* (2013.01); *H10K 50/00* (2023.02); *C08L 2203/16* (2013.01); *C08L 2203/20* (2013.01); *G01N 2201/06193* (2013.01)

(58) Field of Classification Search
CPC ....................................... C08L 33/10
See application file for complete search history.

(56) References Cited

U.S. PATENT DOCUMENTS

| | | | |
|---|---|---|---|
| 6,960,878 B2 | 11/2005 | Sakano et al. | |
| 7,923,917 B2 * | 4/2011 | Eida ...................... | H10K 59/38 313/512 |
| 2016/0282267 A1 | 9/2016 | Tanaka et al. | |
| 2017/0267921 A1 | 9/2017 | Shin | |

FOREIGN PATENT DOCUMENTS

| | | | | |
|---|---|---|---|---|
| KR | 10-2007-0066781 A | 6/2007 | | |
| KR | 10-2010-0121494 A | 11/2010 | | |
| KR | 10-2014-0007840 A | 1/2014 | | |
| KR | 1590299 B1 * | 2/2016 | ............... | C07F 5/02 |
| TW | 201643234 A | 12/2016 | | |

OTHER PUBLICATIONS

Machine translation of KR 1590299 B1, published Feb. 1, 2016 <<retrieved from Espacenet on Sep. 23, 2022 >>.*
Search Report and Written Opinion issued for PCT Application No. PCT/KR2018/005766 dated Sep. 7, 2018, 7 pages.

* cited by examiner

*Primary Examiner* — Vickey Nerangis
(74) *Attorney, Agent, or Firm* — ROTHWELL, FIGG, ERNST & MANBECK, P.C.

(57) ABSTRACT

The present application provides a resin composition which effectively inhibits a photobleaching phenomenon as well as realizes excellent external blocking properties and optical properties through the secondary structure transition concentration and relaxation time of the resin composition, a reliability evaluation method thereof, and a color conversion film comprising the same.

3 Claims, 1 Drawing Sheet

[Figure 1]
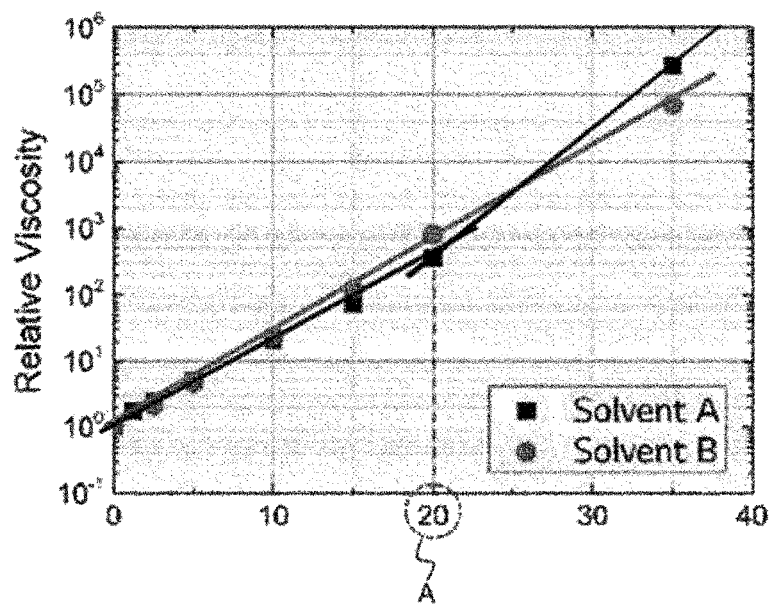
[Figure 2]
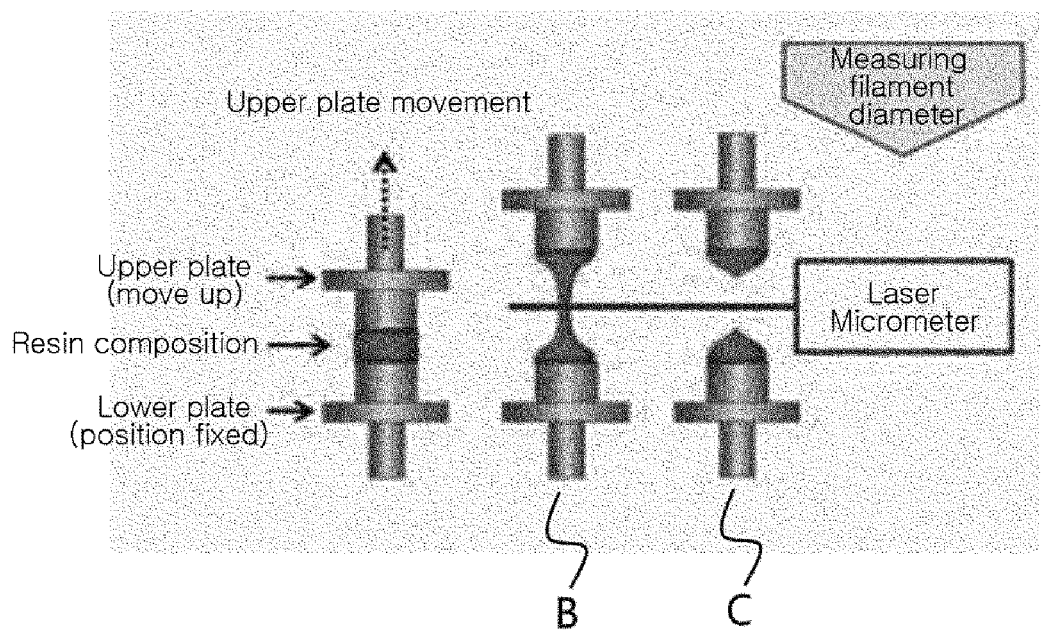

RESIN COMPOSITION AND RELIABILITY EVALUATION METHOD THEREOF AND COLOR CONVERSION FILM COMPRISING THE SAME

CROSS-REFERENCE TO RELATED APPLICATIONS

This application is a 35 U.S.C. 371 National Phase Entry Application from PCT/KR2018/005766, filed May 21, 2018, which claims priority to Korean Patent Application No. 10-2017-0062427 filed on May 19, 2017, the disclosures of which are incorporated herein by reference in their entirety.

TECHNICAL FIELD

The present invention relates to a resin composition, a reliability evaluation method thereof, and a color conversion film comprising the same.

BACKGROUND ART

TVs are becoming high image quality, slimmer and more sophisticated together with area enlargement. High-performance and high-image quality OLED TVs still have a problem of price competitiveness, and accordingly the market is not yet open earnestly. Therefore, efforts to similarly secure advantages of OLEDs with LCDs are continuing.

Conventional LCDs are provided with color conversion films containing dyes for coloring, where many inorganic fluorescent substances have been used as the dyes, but since the inorganic fluorescent substances have a narrow color gamut, there is a problem that a color conversion rate is lowered, and studies to use organic fluorescent substances instead of inorganic fluorescent substances have been recently attempted to improve this problem.

However, most of the organic fluorescent substances are easily oxidized by external factors such as moisture to cause a photobleaching phenomenon, and accordingly have a problem that optical characteristics of the color conversion film are deteriorated.

DISCLOSURE

Technical Problem

The present application provides a resin composition capable of realizing excellent optical characteristics, a reliability evaluation method thereof, and a color conversion film containing the same.

Technical Solution

The present application relates to a reliability evaluation method of a resin composition. The reliability evaluation method may be, for example, a reliability evaluation method for a resin composition applied to light emission of a display device such as an LCD. Furthermore, for example, the cured product of the composition can be applied to a backlight unit of a display device.

An exemplary reliability evaluation method is a reliability evaluation method of a resin composition comprising a polymer resin and an organic fluorescent substance. The resin composition may satisfy Equation 1 below or may have a relaxation time ($\lambda$) of 20 ms or more according to Equation 2.

$$C_E \leq 30 \text{ wt \%} \quad \text{[Equation 1]}$$

$$\frac{D(t)}{D_1} = k\exp\left(-\frac{t}{3\lambda}\right) \quad \text{[Equation 2]}$$

In Equation 1 above, when the relative viscosity of the resin composition is measured according to the concentration of the resin composition at a temperature of 25° C. and a shear rate of 10 s$^{-1}$ and the measurement values are shown in a graph of relative viscosities according to concentrations, $C_E$ represents a concentration at an inflection point of the graph gradient.

In Equation 2 above, in a state where the resin composition is sealed between a pair of circular plates disposed coaxially and vertically at a temperature of 25° C. using an extensional viscometer CaBER and the upper plate is lifted vertically by 40 mm for a time of 50 ms and held as it is, $D_1$ represents the initial diameter of the filament formed by the resin composition, D(t) represents the diameter of the filament at a breakup time (t), and k represents a proportional constant. The proportional constant k may be, for example, a number between −10 and 10.

The inflection point of the graph gradient measured according to the method of Equation 1 above may be one or more, but the term "inflection point" herein means a point that the graph gradient first changes when the concentration of the resin composition is 5 wt % or more.

In Equation 1 above, the fact that a concentration of a resin composition is increased means that the solid content in the resin composition is increased. In addition, the term "relative viscosity" means a relative viscosity measured in comparison with the control group, where the control group may be a solvent having a viscosity of, for example, 0.8 cP. In one example, the solvent having a viscosity of 0.8 cP may have a relative viscosity of 1. Furthermore, the apparatus for measuring the viscosity is not particularly limited, but can be measured using a known rheometer, for example.

In the present application, the term "concentration at the inflection point of the graph" can be used in the same meaning as a secondary structure transition concentration (CE) of the resin composition.

FIG. 1 is a graph showing secondary structure transition concentrations of the resin compositions prepared in Examples and Comparative Examples of the present application, according to Equation 1.

FIG. 2 is a diagram schematically showing a method of measuring a filament diameter using an extensional viscometer CaBER.

Referring to FIG. 1, the secondary structure transition concentration (CE) means the concentration of the resin composition at the inflection point of the A portion.

Referring to B in FIG. 2, $D_1$ in Equation 2 above represents the initial diameter of the filament formed by the resin composition in a state where the upper plate of the extensional viscometer is lifted vertically by 40 mm for a time of 50 ms and held as it is. Referring to C in FIG. 2, the filament formed by the resin composition gradually decreases in diameter over time and is broken, where D(t) represents the diameter immediately before the filament is broken.

Here, the term "initial diameter" means the diameter of the filament formed by the resin composition immediately after the upper plate of the extensional viscometer is lifted vertically by 40 mm for a time of 50 ms. The term "diameter" means the diameter measured at a substantial midpoint between the upper plate and the lower plate, and the "substantial midpoint" means a point including an error range of ±5 mm at the midpoint between the upper plate and the lower plate.

The "breakup time (t)" means the time taken from immediately after the upper plate of the extensional viscometer is lifted vertically by 40 mm to immediately before the filament gradually decreases in diameter over time to be completely broken. The apparatus for measuring the diameter of the filament may be various, and for example, a change in filament diameter can be measured in real time using a laser micrometer.

Also, in this specification, the term "relaxation time ($\lambda$)" means the time taken for the resin composition to return from the breakup time to the equilibrium state. Specifically, when the upper plate is lifted vertically, polymer chains in the resin composition have been unfolded and broken, and then loosened gradually with time to return to the form of the original polymer chains, where the relaxation time means the time taken for the unfolded polymer chains to return to the original form.

In one example, the reliability evaluation method can be performed by comparing solid contents and relaxation times of two or more resin compositions.

In exemplary reliability evaluation criteria, it can be evaluated that as the secondary structure transition concentration ($C_E$) of the resin composition in Equation 1 above is lower or the relaxation time ($\lambda$) according to Equation 2 becomes longer, the resin composition has higher reliability. Furthermore, when such a resin composition is produced as a color conversion film, it can be evaluated that the color conversion film has excellent light resistance.

In one embodiment, the solid content represented by Equation 1 above may be 30 wt % or less, 25 wt % or less, 24 wt % or less, 23 wt % or less, 22 wt % or less, or 21 wt % or less. The lower limit of the solid content is not particularly limited, which may be, for example, 0.001 wt % or more, 0.01 wt % or more, 0.1 wt % or more, or 1.0 wt % or more. In the present application, the term "solid content" is interpreted to be the same as the concentration of the resin composition. In addition, the relaxation time represented by Equation 2 above may be 20 ms or more, 23 ms or more, 25 ms or more, or 26 ms or more. The upper limit of the relaxation time is not particularly limited, which may be, for example, 1000 ms or less, 500 ms or less, or 100 ms or less.

The resin composition of the present application has an advantage that by controlling the respective parameters according to Equation 1 or 2 above in a specific range, an organic fluorescent substance in the polymer resin is uniformly dispersed upon producing a film, whereby the variation of the performance between specific regions is small, and the polymer resin also has excellent ability to protect the organic fluorescent substance from moisture and oxygen, whereby it can prevent the problem that the optical characteristics are lowered by the organic fluorescent substance. Specifically, when the resin composition is produced into a film, the problem that the organic fluorescent substance reacts with moisture and oxygen to cause a photobleaching phenomenon can be minimized, thereby securing the excellent light resistance of the film.

The material constituting the resin composition is not particularly limited as long as the physical properties are satisfied. An exemplary resin composition may comprise a polymer resin and an organic fluorescent substance. In order to adjust the secondary structure transition concentration ($C_E$) of the resin composition represented by Equation 1 above or the relaxation time ($\lambda$) represented by Equation 2 above in the above range, the polymer resin and its solvent can be suitably selected, whereby it is possible to provide a color conversion film having excellent endurance reliability at high temperature and high humidity and capable of easily realizing a desired optical characteristic while realizing excellent moisture barrier performance upon producing a film.

In one example, the polymer resin of the present application may be a thermoplastic resin or a thermosetting resin. The term "thermosetting resin" means a resin that can be cured through an appropriate heat application or aging process.

In the present application, the specific kind of the thermoplastic resin is not particularly limited. In one example, as the thermoplastic resin, for example, poly(meth)acrylic series such as polymethylmethacrylate (PMMA), polycarbonate series (PC), polystyrene series (PS), polyarylene series (PAR), polyurethane series (TPU), styrene-acrylonitrile series (SAN), polyvinylidene fluoride series (PVDF), polyvinyl alcohol series (PVA), modified polyvinylidene fluoride series (modified-PVDF) and the like may be used. One or two or more of these resins may be included.

In one example, the thermoplastic resin may be a poly(meth)acrylic polymer in consideration of excellent interaction with the kinds of solvents described below. An example of (meth)acrylic acid ester monomers constituting the poly(meth)acrylic polymer is as follows. In this specification, the term "(meth)acrylic" may mean acrylic or methacrylic. The (meth)acrylic acid ester monomer can be exemplified by an alkyl (meth)acrylate, and for example, can be exemplified by an alkyl (meth)acrylate having an alkyl group with 1 to 20 carbon atoms, such as methyl (meth)acrylate, ethyl (meth)acrylate, n-propyl (meth)acrylate, isopropyl (meth)acrylate, n-butyl (meth)acrylate, t-butyl (meth)acrylate, sec-butyl (meth)acrylate, pentyl (meth)acrylate, hexyl (meth)acrylate, 2-ethylhexyl (meth)acrylate, 2-ethylbutyl (meth)acrylate, n-octyl (meth)acrylate, isooctyl (meth)acrylate, isononyl (meth)acrylate, lauryl (meth)acrylate or tetradecyl (meth)acrylate, and the like. The alkyl (meth)acrylate may have 1 to 20, 1 to 15, 1 to 10, 1 to 8, 1 to 5, or 1 to 3 carbon atoms in the alkyl group, but is not limited thereto.

In addition, the poly(meth)acrylic polymer of the present application may include a polymer comprising (meth)acrylic acid as a monomer, in addition to the alkyl (meth)acrylate. In one example, the polymer resin of the present application may be a mixture of a polymer containing the alkyl (meth)acrylate as a polymerization unit and a polymer containing the (meth)acrylic acid as a polymerization unit. In the case of the mixture, the polymer containing (meth)acrylic acid as a polymerization unit may be included in an amount of 50 to 150 parts by weight, 60 to 140 parts by weight, 70 to 130 parts by weight, 75 to 125 parts by weight, 83 to 118 parts by weight or 88 to 110 parts by weight, relative to 100 parts by weight of the polymer containing the alkyl (meth)acrylate as a polymerization unit.

In an embodiment of the present application, the thermoplastic resin may have a weight average molecular weight in a range of about 100,000 to 2,000,000, 150,000 to 1,500,000 or 300,000 to 1,000,000. The thermosetting resin may have a weight average molecular weight in a range of about 100,000 to 2,000,000, 150,000 to 1,500,000 or 300,000 to 1,000,000. The term "weight average molecular weight" herein means a value converted to the standard polystyrene measured by GPC (gel permeation chromatograph).

In one example, the thermosetting resin is not particularly limited as long as it satisfies the characteristic ranges shown in the above-mentioned Equation 1 or 2. In one example, the thermosetting resin may comprise at least one thermosetting functional group. For example, it may comprise at least one heat-curable functional group such as an epoxy group, a glycidyl group, an isocyanate group, a hydroxyl group, a carboxyl group or an amide group as one which can be cured to exhibit an adhesive property. A specific kind of such a resin may include an acrylic resin, a polyester resin, an isocyanate resin, an ester resin, an imide resin or an epoxy resin, and the like, but is not limited thereto.

In an embodiment of the present application, the resin composition may further comprise a curing agent. For example, it may further comprise a heat curing agent capable of reacting with the thermosetting resin to form a cross-linked structure or the like.

In one example, an appropriate type of curing agent may be selected and used depending on the type of the functional group contained in the resin. In one example, the heat curing agent may include an amine curing agent, an imidazole curing agent, a phenol curing agent, a phosphorus curing agent, a triazine curing agent, a thiol-based curing agent, an isocyanuric acid-based curing agent or an acid anhydride curing agent.

In the present application, the organic fluorescent substance is not particularly limited as long as it is an organic material capable of containing a fluorescent component to emit light by stimulation with light, and having light resistance, which may include, for example, a polyaromatic hydrocarbon, such as naphthalene, anthracene, naphthacene, pentacene, perylene, terylene, quaterylene, phenanthrene and pyrene, which can be substituted with, for example, a hydroxyl group, an amino group, a carboxyl group or a halogen element; a heterocyclic compound derivative such as pyridine, quinoline, acridine, indole, tryptophan, carbazole, dibenzofuran, dibenzothiophene, xanthene, rhodamine, pyronine, fluorescein, eosin and coumarin, and the like.

In one example, the organic fluorescent substance may be Alexa 350, Alexa 430, AMCA, BODIPY 630/650, BODIPY 650/665, BODIPY-FL, BODIPY-R6G, BODIPY-TMR, BODIPY-TRX, Cascade Blue, Cy3, Cy5, 6-FAM, fluorescein isothiocyanate, HEX, 6-JOE, Oregon Green 488, Oregon Green 500, Oregon Green 514, Pacific Blue, REG, Rhodamine Green, Rhodamine Red, Renographin, ROX, TAMRA, TET, tetramethylrhodamine or Texas Red.

In one embodiment, the organic fluorescent substance may be included in an amount of 0.1 to 10 parts by weight, 0.5 to 5 parts by weight, 1 to 4 parts by weight or 1.5 to 3 parts by weight, relative to 100 parts by weight of the polymer resin.

The resin composition in the present application may further comprise a solvent. The solvent may be a solvent which exhibits excellent interaction depending on the kind of the polymer resin as described above, which can be selected through Equation 1 or 2. For example, the solvent may be one or two or more selected from the group consisting of toluene, xylene, acetone, chloroform, various alcohol-based solvents, MEK (methyl ethyl ketone), MIBK (methyl isobutyl ketone), EA (ethyl acetate), butyl acetate, DMF (dimethylformamide), DMAc (dimethylacetamide), DMSO (dimethylsulfoxide), NMP (N-methyl-pyrrolidone), cyclohexanone, PGMEA (propylene glycol methylethyl acetate) and dioxane, and the resin composition of the present application may select and comprise a solvent which satisfies Equation 1 or 2 depending on the kind of the polymer resin.

The solvent may be included in an amount of 100 parts by weight to 500 parts by weight, 150 parts by weight to 450 parts by weight, 200 parts by weight to 400 parts by weight or 250 parts by weight to 350 parts by weight, relative to 100 parts by weight of the polymer resin, but is not limited thereto.

In one example, the resin composition of the present application comprises a polymer resin, an organic fluorescent substance and a solvent, but it is important that the respective components are selected in consideration of the interaction between the three components, and accordingly, it is possible to determine reliability such as mixing characteristics, dispersibility and light resistance after curing among the three components through whether or not the parameter according to Equation 1 or 2 as described above satisfies a specific range.

For example, when the interaction between the polymer components in the polymer resin is stronger than the interaction between the polymer resin and the solvent, the polymer components may tend to agglomerate even if the resin composition is mixed with the solvent. In another example, even if the content of the polymer resin in the composition is excessively high, the polymer components may tend to agglomerate. This tendency may cause a photobleaching phenomenon by forming cracks in a color conversion film to be described below and reacting the organic fluorescent substance and oxygen or moisture introduced into the cracks. That is, when the interaction between the polymer resin and the solvent is weak, the secondary structure transition concentration of Equation 1 or the relaxation time of Equation 2 does not satisfy the above-mentioned specific range in the resin composition and the color conversion film comprising them.

On the other hand, when the interaction between the polymer resin and the solvent is strong, the dispersibility is excellent even if the polymer resin is formulated in the composition at a high content, and when it is produced into a color conversion film to be described below, the problem, in which the optical characteristics by the organic fluorescent substance are lowered, can be prevented because of excellent blocking properties.

The present application also relates to a resin composition. The resin composition may be a resin composition which is evaluated as excellent in dispersibility and light resistance according to the reliability evaluation method as described above.

The exemplary resin composition comprises a polymer resin and an organic fluorescent substance, which may satisfy Equation 1 below or may have a relaxation time ($\lambda$) of 20 ms or more according to Equation 2.

$$C_E \leq 30 \text{ wt \%} \quad \text{[Equation 1]}$$

$$\frac{D(t)}{D_1} = k\exp\left(-\frac{t}{3\lambda}\right) \quad \text{[Equation 2]}$$

In Equation 1 above, when the relative viscosity of the resin composition is measured according to the concentration of the resin composition at a temperature of 25° C. and a shear rate of 10 s$^{-1}$ and the measurement values are shown in a graph of relative viscosities according to concentrations, $C_E$ represents a concentration at an inflection point of the graph gradient.

In Equation 2 above, in a state where the resin composition is sealed between a pair of circular plates disposed coaxially and vertically at a temperature of 25° C. using an extensional viscometer CaBER and the upper plate is lifted vertically by 40 mm for a time of 50 ms and held as it is, $D_1$ represents the initial diameter of the filament formed by the resin composition, D(t) represents the diameter of the filament at a breakup time (t), and k represents a proportional constant. The proportional constant k may be, for example, a number between −10 and 10.

The present application also relates to a color conversion film. An exemplary color conversion film may have a color conversion layer comprising the above-described resin composition. The color conversion film comprises the resin composition having the secondary structure transition concentration or the relaxation time in the specific range as described above, whereby the excellent external blocking property of the color conversion layer can be realized to prevent the performance degradation of the organic fluorescent substance. Specifically, the polymer resin constituting the color conversion layer has excellent ability to protect the organic fluorescent substance from moisture and oxygen by forming a structure showing low oxygen permeability and low moisture permeability, whereby it can prevent the problem of causing a photobleaching phenomenon by reacting the organic fluorescent substance and the moisture or oxygen.

The color conversion film of the present application may further comprise a protective film or a barrier film on at least one side of the color conversion layer. As the protective film and barrier film, those known in the art can be used, and for example, a polyethylene terephthalate (PET) film can be used.

The present application also relates to a backlight unit comprising the above-mentioned color conversion film. The backlight unit may have a backlight unit configuration known in the art, except for comprising the color conversion film.

An exemplary backlight unit comprises a side-chain type light source, a reflective plate surrounding the light source, a light guide plate for guiding light directly emitted from the light source or reflected from the reflective plate, a reflective layer provided on one side of the light guide plate and a color conversion film provided on a side opposite to the side facing the reflective layer of the light guide plate. In addition, the light source may also be used as a direct-type as well as a side-chain type, and the reflective plate or the reflective layer may also be omitted or replaced with another structure as needed, and additional films, such as a light diffusion film, a condensing film or a luminance enhancement film, can be further provided, if necessary.

Advantageous Effects

The present application provides a resin composition which effectively inhibits a photobleaching phenomenon as well as realizes excellent external blocking properties and optical properties through the secondary structure transition concentration and relaxation time of the resin composition, a reliability evaluation method thereof, and a color conversion film comprising the same.

BRIEF DESCRIPTION OF DRAWINGS

FIG. 1 is a graph showing secondary structure transition concentrations of the resin compositions prepared in Examples and Comparative Examples of the present application, according to Equation 1.

FIG. 2 is a diagram schematically showing a method of measuring a filament diameter using an extensional viscometer CaBER.

BEST MODE

Hereinafter, the present invention will be described in more detail through Examples according to the present invention and Comparative Examples not according to the present invention, but the scope of the present invention is not limited by the following examples.

Example 1

(1) Preparation of Resin Composition

To a sealable 500 mL reaction vessel, 74.5 parts by weight of dimethylformamide (DMF, Sigma Aldrich), 0.5 part by weight of BODIPY-FL (Thermo Fisher) and 25 parts by weight of a mixture that polymethylmethacrylate and polymethacrylic acid were mixed in a weight ratio of 5:5 were introduced, and stirred at room temperature for about 1 hour to prepare a uniform resin composition.

(2) Production of Color Conversion Film

The resin composition prepared above was applied to the release surface of the releasing PET and dried (5 atm) in an oven at 130° C. for 3 minutes to produce a color conversion film comprising a color conversion layer having a thickness of 50 μm. For a sample that the produced film was irradiated with ultraviolet rays at 2 J/cm$^2$ (100 mW/cm$^2$ on the basis of A region) under a nitrogen atmosphere, physical properties were measured.

(3) Measurement of Secondary Structure Transition Concentration ($C_E$)

Depending on the concentration (solid content) of the resin composition prepared in Example 1, the relative viscosity of the resin composition was measured. When the measured relative viscosities depending on the concentrations were plotted, the solid content at the inflection point of the graph gradient was measured. The viscosity was measured using a viscoelasticity meter (dynamic hybrid rheometer, DHR, TA Instruments) under a shear rate condition of 10 s$^{-1}$ at 25° C., and the relative viscosity was calculated by comparing the measured viscosity with the control sample having a viscosity of 0.8 cP, and the results were shown in FIG. 1. Referring to FIG. 1, Solvent A represents dimethylformamide (DMF) used as a solvent in Example 1.

Example 2

(1) Preparation of Resin Composition

To a sealable 500 mL reaction vessel, 74.5 parts by weight of dimethylformamide (DMF, Sigma Aldrich), 0.5 part by weight of BODIPY-FL (Thermo Fisher) and 25 parts by weight of a mixture that polymethylmethacrylate and polymethacrylic acid were mixed in a weight ratio of 5:5 were introduced, and stirred at room temperature for about 1 hour to prepare a uniform resin composition.

(2) Production of Color Conversion Film

The resin composition prepared above was applied to the release surface of the releasing PET and dried (5 atm) in an oven at 130° C. for 3 minutes to produce a color conversion film comprising a color conversion layer having a thickness of 50 μm. For a sample that the produced film was irradiated with ultraviolet rays at 2 J/cm$^2$ (100 mW/cm$^2$ on the basis of A region) under a nitrogen atmosphere, physical properties were measured.

(3) Relaxation Time (λ) Measurement

As shown in FIG. 2, for the resin composition solution prepared in Example 2, the relaxation time was measured using an extensional viscometer CaBER. The resin composition was sealed between a pair of circular plates disposed coaxially and vertically at a temperature of 25° C. The diameter of the filament formed by the resin composition was measured in real time using a laser micrometer in a state where the upper plate was lifted vertically by 40 mm for a time of 50 ms and held as it was. When the results were shown as a graph of diameter change with time, the gradient at the breakup time was measured and the relaxation time (λ)

was measured according to the above-described Equation 2. The relaxation time was calculated using an MATLAB program.

Comparative Example 1

A resin composition and a color conversion film were produced in the same manner as in Example 1, except that propylene glycol methyl ethyl acetate (PGME) was used instead of dimethyl formamide (DMF).

For the resin composition, the secondary structure transition concentration ($C_E$) was measured as in Example 1, and the results were shown in FIG. 1. Referring to FIG. 1, Solvent B represents propylene glycol methyl ethyl acetate (PGME) used as a solvent in Comparative Example 1.

Comparative Example 2

A resin composition and a color conversion film were produced in the same manner as in Example 1, except that tetrahydrofuran (THF) was used instead of dimethylformamide (DMF).

For the resin composition, the secondary structure transition concentration ($C_E$) was measured as in Example 1.

Comparative Example 3

A resin composition and a color conversion film were produced in the same manner as in Example 1, except that propylene glycol methyl ethyl acetate (PGME) was used instead of dimethyl formamide (DMF).

For the resin composition, the relaxation time ($\lambda$) was measured as in Example 2.

Comparative Example 4

A resin composition and a color conversion film were produced in the same manner as in Example 1, except that tetrahydrofuran (THF) was used instead of dimethylformamide (DMF).

For the resin composition, the relaxation time ($\lambda$) was measured as in Example 2.

The measurement results were summarized and described in Tables 1 and 2 below.

TABLE 1

|  | Example 1 | Comparative Example 1 | Comparative Example 2 |
|---|---|---|---|
| Secondary structure transition concentration ($C_E$) | 20 wt % | >30 wt % | >30 wt % |

TABLE 2

|  | Example 2 | Comparative Example 3 | Comparative Example 4 |
|---|---|---|---|
| Relaxation time ($\lambda$) | 27 ms | 17 ms | 14 ms |

In Examples and Comparative Examples above, when the polymer resins were polymethylmethacrylate and polymethacrylic acid, it was evaluated whether Equation 1 or 2 was satisfied as the solvent type was changed, whereby the solvent suitable for the specific polymer resin could be selected.

As to the light resistance evaluation of the color conversion films produced in Examples and Comparative Examples, as the secondary structure transition concentration ($C_E$) of the resin composition was lower and the relaxation time was longer, excellent light resistance was shown.

The invention claimed is:

1. A resin composition comprising a polymer resin, a solvent and an organic fluorescent substance, and satisfying Equation 1 below or having a relaxation time ($\lambda$) of 20 ms or more according to Equation 2 below,
   wherein the polymer resin comprises (meth)acrylic acid and alkyl (meth)acrylate as a monomer, and
   wherein the solvent comprises dimethylformamide:

$$C_E \leq 30 \text{ wt \%} \quad \text{[Equation 1]}$$

$$\frac{D(t)}{D_1} = k\exp\left(-\frac{t}{3\lambda}\right) \quad \text{[Equation 2]}$$

in the Equation 1, when a relative viscosity of the resin composition is measured according to a plurality of concentration of the resin composition at a temperature of 25° C. and a shear rate of 10 s$^{-1}$, plotting the measurement viscosities against the plurality of concentrations on a line graph, $C_E$ represents a concentration at an inflection point of the line graph, and
   in the Equation 2, where the resin composition is sealed between a pair of circular plates disposed coaxially and vertically at a temperature of 25° C. using an extensional viscometer and the upper plate is lifted vertically by 40 mm and held for a time of 50 ms to form a filament, $D_1$ represents an initial diameter of the filament formed by the resin composition immediately after the upper plate of the extensional viscometer is lifted vertically by 40 mm for a time of 50 ms, D(t) represents a diameter of the filament at a breakup time (t) wherein the breakup time is the time taken from immediately after the upper plate of the extensional viscometer is lifted vertically by 40 mm to immediately before the filament is completely broken and wherein the diameter is measured at a substantial midpoint between the upper plate and the lower plate and the substantial midpoint is a point including an error range of ±5 mm at the midpoint between the upper plate and the lower plate, and k represents a proportional constant.

2. A color conversion film having a color conversion layer comprising the resin composition of claim 1.

3. The color conversion film according to claim 2, further comprising a protective film or a barrier film on at least one side of the color conversion layer.

* * * * *